(12) United States Patent
Satake

(10) Patent No.: US 8,647,339 B2
(45) Date of Patent: Feb. 11, 2014

(54) BALLOON CATHETER SYSTEM

(75) Inventor: Shutaro Satake, Kamakura (JP)

(73) Assignee: Japan Electel Inc., Tokyo (JP)

( * ) Notice: Subject to any disclaimer, the term of this patent is extended or adjusted under 35 U.S.C. 154(b) by 317 days.

(21) Appl. No.: 12/921,595

(22) PCT Filed: Dec. 19, 2008

(86) PCT No.: PCT/JP2008/073214
§ 371 (c)(1),
(2), (4) Date: Sep. 9, 2010

(87) PCT Pub. No.: WO2010/070766
PCT Pub. Date: Jun. 24, 2010

(65) Prior Publication Data
US 2011/0264085 A1    Oct. 27, 2011

(51) Int. Cl.
*A61B 18/18*  (2006.01)

(52) U.S. Cl.
USPC ............................................. 606/33; 606/41

(58) Field of Classification Search
USPC ...................................................... 606/28–45
See application file for complete search history.

(56) References Cited

U.S. PATENT DOCUMENTS

| | | | | |
|---|---|---|---|---|
| 5,451,220 A * | 9/1995 | Ciervo | | 606/1 |
| 5,480,417 A * | 1/1996 | Hascoet et al. | | 607/101 |
| 2001/0005791 A1 | 6/2001 | Ginsburg | | |
| 2003/0065371 A1 | 4/2003 | Satake | | |
| 2004/0044334 A1 | 3/2004 | Lafontaine | | |
| 2005/0182396 A1 | 8/2005 | Lafontaine | | |
| 2007/0060990 A1 * | 3/2007 | Satake | | 607/101 |

FOREIGN PATENT DOCUMENTS

| | | |
|---|---|---|
| EP | 1946712 A1 | 7/2008 |
| JP | 2005074104 | 3/2005 |
| JP | 2006198209 | 8/2006 |

OTHER PUBLICATIONS

European Search Report dated Oct. 15, 2012, in connection with corresponding European Application No. 08878934.2 (PCT/JP2008/073214).

* cited by examiner

*Primary Examiner* — Linda Dvorak
*Assistant Examiner* — Amanda Scott
(74) *Attorney, Agent, or Firm* — Duane Morris LLP; J. Rodman Steele, Jr.; Gregory M. Lefkowitz

(57) ABSTRACT

It is an object of the present invention to provide a radiofrequency thermal balloon catheter system capable of precisely predicting the surface temperature of a balloon which directly heats a target tissue without allowing a temperature sensor to directly contact with a balloon membrane. In the radiofrequency thermal balloon catheter system, a vibrational wave W is applied to an inside of the balloon 6 through a solution transport path 11 by means of a vibration generator 42. An in-balloon temperature sensor 8 is insulated from the electrode 7 for delivery of radiofrequency current to be fixed in the vicinity of a distal end of an inner tube 3 and then the temperature of the swirls S flowing along the inner surface of the balloon 6 is detected. In the present system, the surface temperature of the balloon 6 can be predicted by measuring the temperature of the swirls S approximate to the surface temperature of the balloon 6 by means of the in-balloon temperature sensor 8 while applying a radiofrequency current.

8 Claims, 10 Drawing Sheets

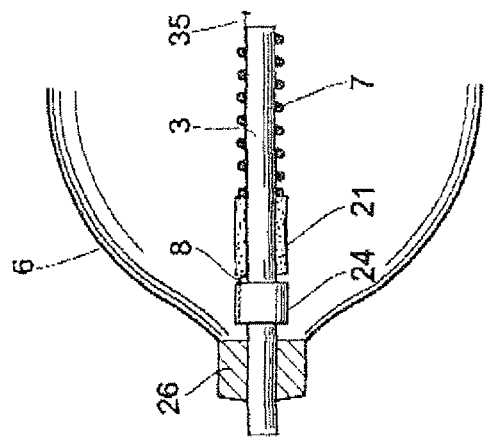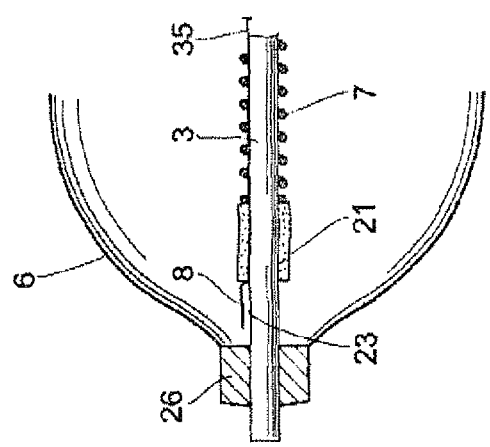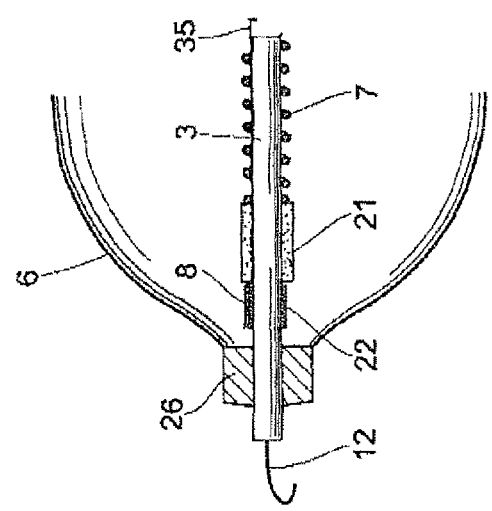

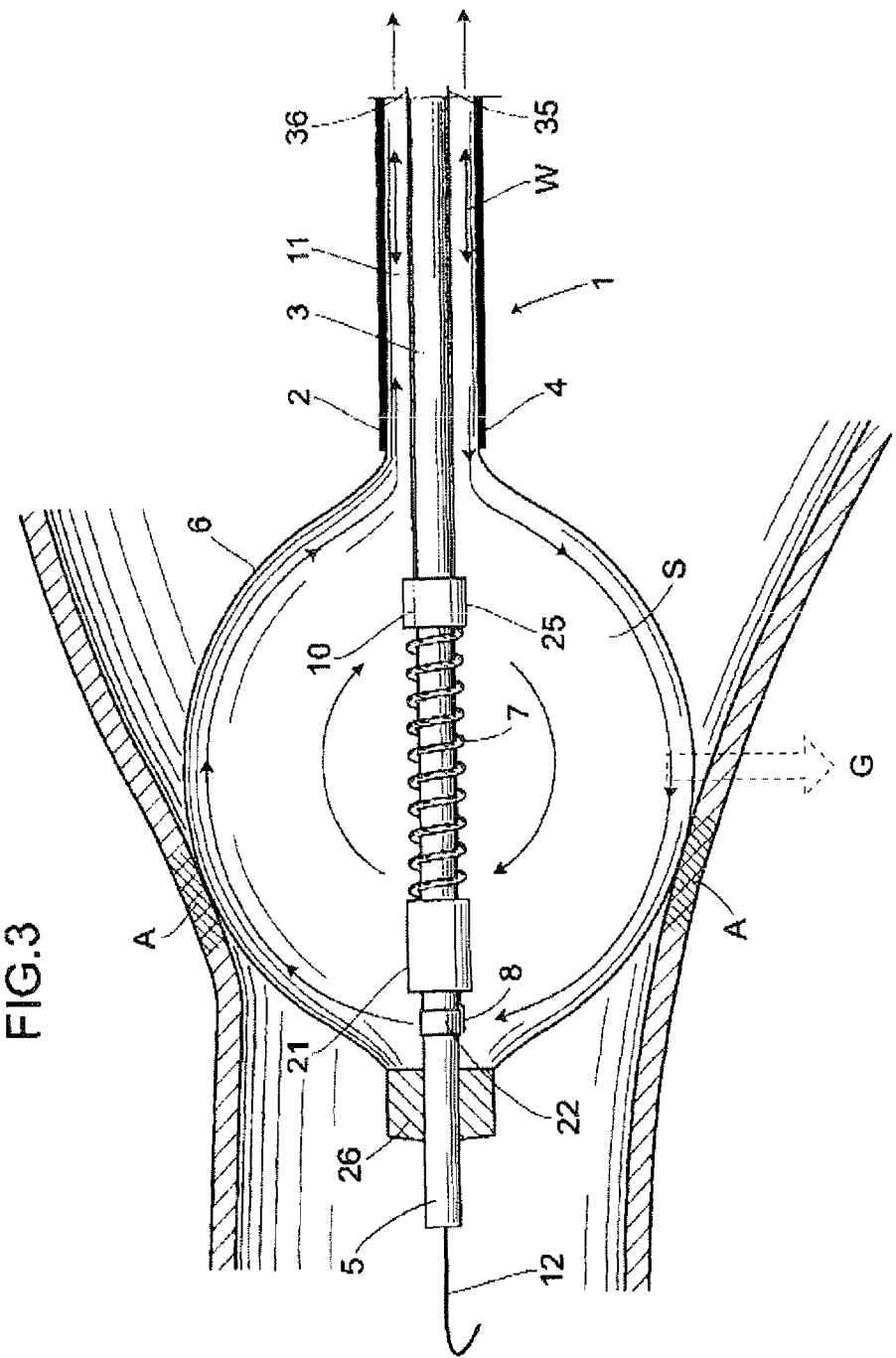

BALLOON CATHETER SYSTEM

CROSS-REFERENCE TO RELATED APPLICATIONS

This application is a §371 national stage entry of International Application No. PCT/JP2008/073214, filed Dec. 19, 2008, the entirety of which is hereby incorporated by reference.

BACKGROUND OF THE INVENTION

1. Technical Field

The present invention relates to a balloon catheter system, particularly to a balloon catheter system employed for a thermal therapy used for ablating, at appropriate temperatures, a source origin of arrhythmia, an unstable atherosclerotic lesion, proliferated smooth muscles which cause bronchial asthma, cancer tissues or the like.

2. Background Art

As a therapeutic modality for treating lesions such as the origin of arrhythmia, atherosclerosis or the like, using a balloon catheter system (e.g., refer to patent documents 1, 2), one has been known in which the tissue in contact with the balloon is subjected to thermal treatment. This balloon catheter system is equipped with a balloon provided with an electrode for delivery of radiofrequency current therein. A radiofrequency current is applied to the electrode for delivery of radiofrequency current and thereby an inside of the balloon is heated to raise a surface temperature of the balloon and then the tissue in contact with the balloon is directly ablated. A tissue depth ablated by the balloon (when the tissue temperature is at 45 degrees or more) is proportional to the surface temperature of the balloon and the delivery time of radiofrequency current and therefore it is of extreme importance to predict the surface temperature of the balloon (FIG. 6).

DISCLOSURE OF THE INVENTION

Problems to be Solved by the Invention

The temperature sensor of the traditional balloon catheter system, however, was arranged in the vicinity of the electrode for delivery of radiofrequency current. Hence, there was a significant difference between a measured temperature indicated by a temperature sensor and a surface temperature of the balloon in contact with tissue. Then, there was the problem that the larger the size of a balloon, the larger the difference between the temperatures. Besides, the temperature rise at the surface of the balloon lagged behind that at the electrode for delivery of radiofrequency current, thus making it difficult to predict the surface temperature of the balloon (FIG. 5).

Further, in order to solve the problems like these, an example is generally known in which as shown in FIG. 10, a temperature sensor 108 is set in contact with an inner surface of a balloon 106. Here, numeral 107 denotes an electrode for delivery of radiofrequency current and lead wires 135 of the temperature sensor 108 are allowed to pass through a portion between an outer tube 102 and an inner tube 103 to be connected to a thermometer, not shown, externally arranged. There has been, however, the problem that the temperature sensor 108 was allowed to contact with the balloon 106 and therefore the balloon 106 became voluminous, leading to difficulty in manipulation. Further problem was presented that a pinhole was prone to be produced in a position where the balloon 106 contacted with the temperature sensor 108.

With the view of the above problems, it is, therefore, an object of the present invention to provide a balloon catheter system capable of precisely detecting a surface temperature of a balloon without allowing the balloon to contact with the temperature sensor.

Patent document 1: Japanese unexamined patent application publication No. 2005-177293
Patent document 2: Japanese unexamined patent application publication No. 2008-167958

Means for Solving the Problem

In order to attain the above object, a first aspect of the present invention is a balloon catheter system comprising: a catheter shaft comprising an outer tube and an inner tube which are slidable to each other, a balloon provided between a distal end of said outer tube and a vicinity of a distal end of said inner tube, an electrode for delivery of radiofrequency current provided in a central portion of said balloon, an external radiofrequency generator which supplies radiofrequency energy to said electrode for delivery of radiofrequency current through a lead wire to heat said balloon; an external thermometer which detects a temperature through a lead wire of a temperature sensor via said temperature sensor provided inside said balloon and its lead wires; a solution transport path formed between said outer tube and said inner tube, in communication with an inside of said balloon; an external vibration generator which applies vibrational waves to said balloon through said solution transport path to generate swirls inside said balloon and thereby makes the temperature inside said balloon uniform; and a guide wire which guides said balloon to a target site, wherein said temperature sensor is separated from said electrode for delivery of radiofrequency current and is fixed to the distal end of said inner tube inside said balloon to detect the temperature of swirls flowing along an inner surface of said balloon.

A second aspect of the present invention is a balloon catheter system, wherein a heat insulating material is interposed between said temperature sensor and said electrode for delivery of radiofrequency current.

A third aspect of the present invention is a balloon catheter system, wherein a heat insulating material is interposed between said temperature sensor and said inner tube.

A fourth aspect of the present invention is a balloon catheter system, wherein a heat insulating space is provided between said temperature sensor and said inner tube.

A fifth aspect of the present invention is a balloon catheter system, wherein said temperature sensor is formed into a tubular shape encircling an entire circumference of said inner tube or is equipped with a tubular good thermal conductor encircling the entire circumference of said inner tube and besides is connected with said tubular good thermal conductor.

A sixth aspect of the present invention is a balloon catheter system, wherein said electrode for delivery of radiofrequency current is monopolar or a bipolar, and when monopolar, a radiofrequency current is applied across said electrode and a counter electrode externally provided, while when bipolar, a radiofrequency current is applied across both electrodes.

A seventh aspect of the present invention is a balloon catheter system, wherein an electrode temperature sensor which detects the temperature of said electrode for delivery of radiofrequency current is provided and said sensor is covered with an insulation material.

An eighth aspect of the present invention is a balloon catheter system, wherein a balloon external heat shield knob is arranged in the vicinity of the distal end of said tube, in contact with an outer surface of said balloon.

A ninth aspect of the present invention is a balloon catheter system, wherein as substitute for said electrode for delivery of radiofrequency current and said external radiofrequency generator, said balloon catheter system is equipped with any one of couples of an ultrasonic heating element and an ultrasonic generator, a laser heating element and a laser generator, a diode heating element and a diode power supply, and a nichrome wire heating element and a nichrome wire power supply unit.

Effects of the Invention

According to the balloon catheter system of the present invention, when a vibrational wave with a suitable frequency (e.g., 25 Hz) and a suitable waveform (e.g., an asymmetric pulse wave) is applied to an inside of the balloon by means of the external vibration generator, large swirls running vertically in relation to gravity are generated inside the balloon under the influence of gravity to cancel a temperature gradient due to convective heat. Besides, the temperature sensor is fixed to the distal end of the inner tube inside the balloon so as to make it possible to detect the temperature of the swirls flowing along the inner surface of the balloon. The temperature of the swirls flowing along the inner surface of the balloon is approximate to the surface temperature of the balloon. Hence, by detecting the temperature of the swirls flowing along the inner surface of the balloon, the surface temperature of the balloon which directly heats a target tissue can be precisely predicted without allowing the temperature sensor to directly contact with the balloon.

Further, the heat insulating material is interposed between the temperature sensor and the electrode for delivery of radiofrequency current. Hence, the temperature sensor can be prevented from being directly heated by the electrode for delivery of radiofrequency current, permitting the temperature of the swirls approximate to the surface temperature of the balloon to be precisely detected.

Furthermore, the heat insulating material is interposed between the temperature sensor and the inner tube. Hence, even if the guide wire passing through the inside of the inner tube is heated by radiofrequency electromagnetic coupling, the surface temperature of the balloon can be precisely detected by preventing the influence of the heat resulting from the radiofrequency electromagnetic coupling.

Moreover, a heat insulating space is provided between the temperature sensor and the inner tube. Hence, even if the guide wire passing through the inside of the inner tube is heated by radiofrequency electromagnetic coupling, the temperature of the swirls approximate to the surface temperature of the balloon can be precisely detected by preventing the influence of the heat resulting from the radiofrequency electromagnetic coupling.

Besides, the temperature sensor is formed into a tubular shape encircling the entire circumference of the inner tube or is equipped with the tubular good thermal conductor encircling the entire circumference of the inner tube and besides is connected with the tubular good thermal conductor. Hence, by means of detecting temperature from the entire circumference of inner tube, the temperature of the swirls approximate to the surface temperature of the balloon can be precisely detected.

Further, the electrode for delivery of radiofrequency current is monopolar or bipolar. Hence, when monopolar, a radiofrequency current is applied across said electrode and the counter electrode externally provided and when bipolar, a radiofrequency current is applied across both electrodes. Hence, the electrode for delivery of radiofrequency current can be heated.

Furthermore, the electrode temperature sensor is provided which detects the temperature of the electrode for delivery of radiofrequency current and further is covered with the heat insulating material. Hence, the temperature of the electrode for delivery of radiofrequency current can be precisely detected without being affected by the swirls.

Moreover, in the vicinity of the distal end of the inner tube, the balloon external heat shield knob is provided in contact with the outer surface of the balloon. Hence, the influence of temperature of blood or the like in contact with the balloon is prevented and thereby the temperature of the swirls approximate to the surface temperature of the balloon can be precisely detected Besides, as substitute for the electrode for delivery of radiofrequency current and the external radiofrequency generator, there is provided any one of couples of an ultrasonic heating element and an ultrasonic generator, a laser heating element and a laser generator, a diode heating element and a diode power supply unit, and a nichrome wire heating element and a nichrome wire power supply unit. Hence, various types of energy can be utilized for heating.

BRIEF DESCRIPTION OF THE DRAWING

FIG. 2 is a partially enlarged view in the vicinity of a distal end of an inner tube illustrating one embodiment of a balloon catheter system according to the present invention.

FIG. 3 is a partially enlarged view in a vicinity of the balloon illustrating a usage state in one embodiment of a balloon catheter system according to the present invention.

BEST MODE FOR CARRYING OUT THE INVENTION

As follows is a detailed description of embodiments of a balloon catheter system according to the present invention with reference to the appended drawings.

Embodiment 1

Figure 1:
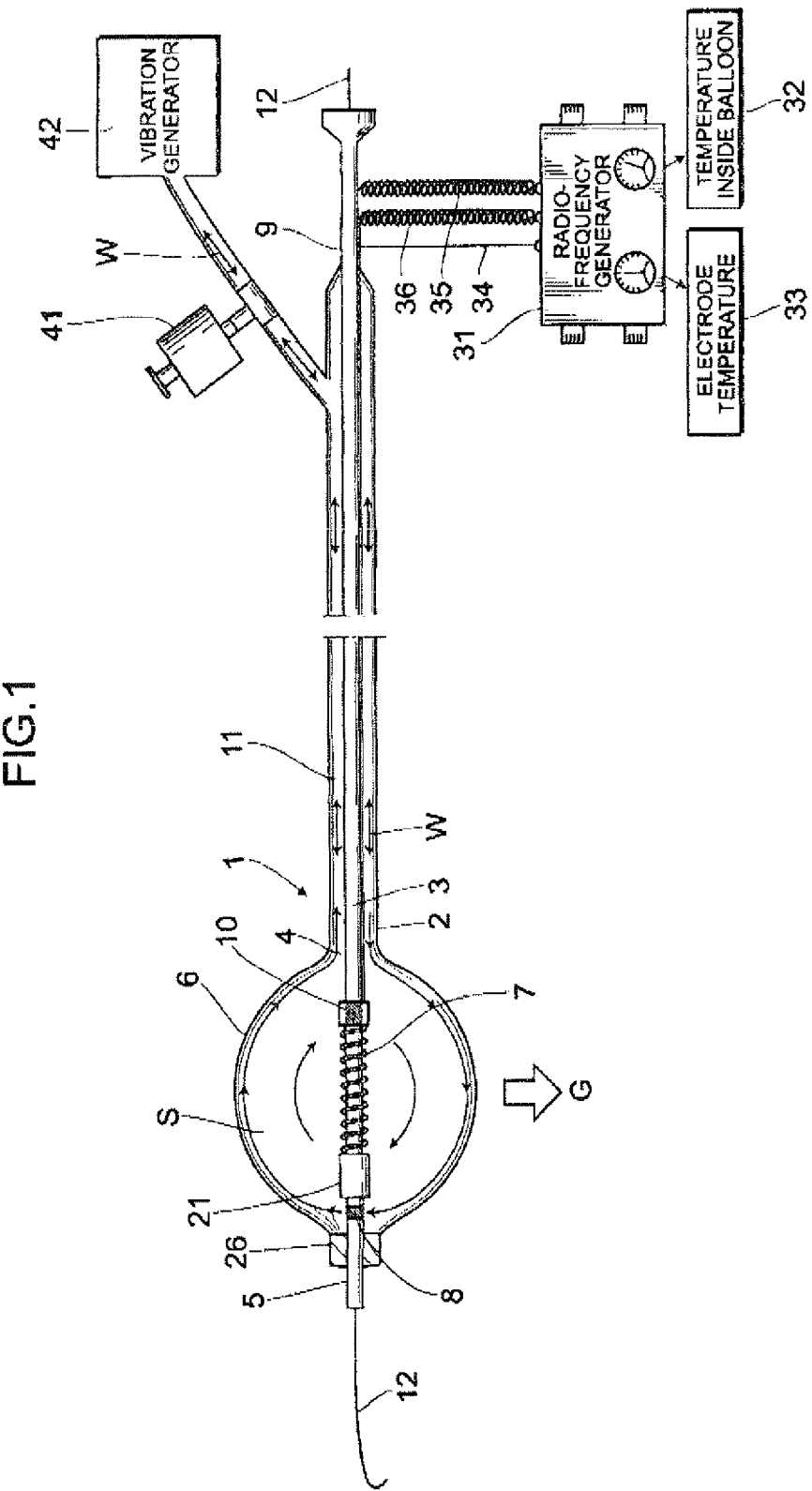
FIG. 1 is an overall view illustrating one embodiment of a balloon catheter system according to the present invention.

FIGS. 1 to 3 show one embodiment of a balloon catheter system according to the present invention. Numeral 1 denotes a catheter shaft, which comprises an outer tube 2 and an inner tube 3 which are slidable to each other. A balloon 6 is provided between a distal end 4 of the outer tube 2 and a vicinity of a distal end 5 of the inner tube 3. The balloon 6 is formed from synthetic resin such as polyurethane or the like. The balloon 6 dilates into an approximately spherical form by filling an inside of the balloon 6 with a solution.

Inside the balloon 6, the electrode 7 for delivery of radiofrequency current for heating the inside of the balloon 6 is wound around the inner tube 3 in a coiled fashion to be provided in a central part of the balloon 6. Then, the electrode 7 for delivery of radiofrequency current is monopolar and is able to conduct a radiofrequency current between itself and a counter electrode, not shown, provided outside the catheter shaft 1. Then, the electrode 7 for delivery of radiofrequency current generates heat by applying a radiofrequency current thereto. Alternatively, the electrode 7 for delivery of radiofrequency current may be bipolar to apply a radiofrequency current across both electrodes.

Further, inside the balloon 6, a temperature sensor 8 for detecting the temperature inside the balloon 6 is fixed in the vicinity of the distal end 5 of the inner tube 3. Besides, an electrode temperature sensor 10 for detecting the temperature of the electrode 7 for delivery of radiofrequency current is arranged in contact with the electrode 7 for delivery of radiofrequency current, and is fixed on a side closer to a proximal end 9 of the inner tube 3.

Between the outer tube 2 and the inner tube 3, a solution transport path 11 is formed which communicates with the inside of the balloon 6. A guide wire 12 for guiding the balloon 6 to a target site is provided in such a fashion as to be inserted through the inner tube 3.

Between the temperature sensor 8 and the electrode 7 for delivery of radiofrequency current, a heat insulating material 21 is interposed. Thus, the temperature sensor 8 can be prevented from being directly heated by the electrode 7 for delivery of radiofrequency current and thus the temperature inside the balloon 6 can be precisely detected. Besides, between the temperature sensor 8 and the inner tube 3, as shown in FIG. 2(a), a heat insulating material 22 is interposed. As a result, even if the guide wire 12 passing through the inner tube 3 is heated by radiofrequency electromagnetic coupling, the temperature sensor 8 can be prevented from being affected by the heat of the guide wire 12, thus permitting the temperature inside the balloon 6 to be precisely detected.

In addition, as shown in FIG. 2(b), as substitute for the heat insulating material 22, a heat insulating space 23 may be provided between the temperature sensor 8 and the inner tube 3. Even in this way, the temperature sensor 8 can be prevented from being affected by the guide wire 12 heated by radiofrequency electromagnetic coupling. Alternatively, as shown in FIG. 2(c), a tubular good thermal conductor 24 encircling an entire circumference of the inner tube 3 may be provided and the temperature sensor 8 may be coupled to this tubular good thermal conductor, otherwise the temperature sensor 8 may be formed into a tubular shape encircling the entire circumference of the inner tube 3. As a result, the temperature inside the balloon 6 can be precisely detected by means of detecting the temperature from the entire circumference of the inner tube 3. Besides, the electrode temperature sensor 10 is covered with an insulating body 25 and therefore can precisely detect the temperature of the electrode 7 for delivery of radiofrequency current without being affected by the swirl S.

In the vicinity of the distal end 5 of the inner tube 3, a balloon external heat shield knob 26 is provided in contact with an outer surface of the balloon 6. As a result, the temperature sensor 8 provided in the vicinity of the distal end 5 of the inner tube 3 inside the balloon 6 can be prevented from being affected by temperature of blood or the like contacting with the balloon 6, thus permitting the temperature inside the balloon 6 to be precisely detected. In addition, the inner tube 3 passes through a central portion of the balloon external heat shield knob 26, which is fixed to the inner tube 3.

Outside the catheter shaft 1, there are provided an external radiofrequency generator 31 for supplying radiofrequency energy for heating the balloon 6 to the electrode 7 for delivery of radiofrequency current, an thermometer 32 for indicating the temperature detected by the temperature sensor 8, and an electrode thermometer 33 for indicating the temperature detected by the electrode temperature sensor 10. The electrode 7 for delivery of radiofrequency current and the external radiofrequency generator 31 are connected electrically to each other through a lead wire 34, while the temperature sensor 8 and the external thermometer 32, the electrode temperature sensor 10 and the electrode thermometer 33 are connected electrically to each other by lead wires 35, 36, respectively. Further, between the distal end 5 of the inner tube 3 and the proximal end 9, the lead wires 34, 35 and 36 are fixed to the inner tube 3.

Furthermore, outside the catheter shaft 1, there are provided a syringe 41 for supplying the solution to the balloon 6 through the solution transport path 11 and a vibration generator 42 for applying asymmetric vibrational waves W the balloon 6 through the solution transport path 11 to steadily generate swirls S inside the balloon 6. Then, a diameter of the balloon 6 is changed by varying pressure of the solution supplied to the balloon 6 by means of the syringe 41. The solution inside the balloon 6 is agitated by the swirls S to keep the temperature inside the balloon 6 uniform.

In addition, in the present embodiment, the electrode 7 for delivery of radiofrequency current fixed to the vicinity of the distal end of the inner tube 3 is employed in order to heat the inside of the balloon 6. Any one capable of heating the inside of the balloon 6, however, may be applicable without confining to a specific device. As substitute for the electrode 7 for delivery of radiofrequency current and the radiofrequency generator 31, any one of couples of an ultrasonic heating element and ultrasonic generator, a laser heating element and laser generator, a diode heating element and diode power supply, and a nichrome wire heating element and nichrome wire power supply unit may be applicable.

Next is a description of how to use the balloon catheter system according to the present embodiment.

First, a liquid containing a physiological saline, a contrast medium or the like are infused from a syringe 41 into a catheter inner cavity, i.e., the solution transport path 11 and the inside of the balloon 6 to thereby perform air bleeding. Then, the balloon 6 is allowed to contract with the outer and inner tubes mutually slid so as to maximize a distance between the distal end 4 of the outer tube 3 and that 5 of the inner tube 3.

Then, by the aid of the guide wire 12, a sheath-shaped guiding sheath for guiding the catheter shaft 1 is inserted into a vicinity of a target site A inside a patient body. Then, the contracted balloon 6 is inserted into the guiding sheath to make the balloon 6 stay in the vicinity of the target site A.

Next, the liquid is infused from the syringe 41 into the balloon 6 to dilate the balloon 6. Here, the balloon 6 is adjusted in length by adjusting the distance between the distal end 4 of the outer tube 2 and the distal end 5 of the inner tube 3 and then the balloon 6 is adjusted in diameter by adjusting pressure of the liquid supplied to the balloon 6 by the syringe 41. Then, the balloon 6 is pressed against the target site A.

Subsequently, the lead wires 34, 35 and 36 each connected to the electrode 7 for delivery of radiofrequency current, the temperature sensor 8 and the electrode temperature sensor 10, respectively, are connected, from the proximal portion 9 of the inner tube 3, to the radiofrequency generator 31, the thermometer 32 and the electrode thermometer 33, respectively. Then, an output of the radiofrequency generator 31 is built up while observing the thermometer 32 and the electrode thermometer 33. Besides, the vibration generator 42 is allowed to start to feed a 2.5 Hz vibrational wave W into the inside of the balloon 6 through the solution transport path 11. Next, the swirl S vertical in relation to the gravity is generated inside the balloon 6 to eliminate a temperature difference resulting from the convection inside the balloon 6.

Here, the temperature sensor 8 is arranged at a position where the swirl S flows in the vicinity of the distal end 5 of the inner tube 3, i.e., in the vicinity of the balloon 6. Hence, the temperature of the swirl S in the vicinity of the balloon 6 can be precisely detected. The temperature of the swirl S in the vicinity of the balloon 6 is substantially constant in a steady state to be approximate to the surface temperature of the balloon 6. Consequently, the surface temperature of the balloon 6 can be almost precisely detected by means of detecting the temperature of the swirl S in the vicinity of the balloon 6.

Then, a target site A in contact with the balloon 6 is ablated while regulating the surface temperature of the balloon 6 and the delivery time of radiofrequency current. Now, as an ablating depth of the tissue of the target site A is proportional to the surface temperature of the balloon 6, by regulating the surface temperature of the balloon 6, the ablated depth can be precisely controlled. Accordingly, specifically in the therapy of atrial fibrillation, the atrial posterior wall containing a pulmonary veins acting as the origin of atrial fibrillation is ablated transmurally in such a manner while an esophagus very close to the atrial posterior wall can be certainly prevented from being injured, thus permitting a safer therapy to be practiced. Besides, the surface temperature of the balloon 6 can be precisely regulated, thus enabling a hyperthermia provided at 43 degree C. for annihilating cancer cells without exerting an irreversible influence on normal tissue and a hyperthermia provided at 43 degree C. for annihilating macrophages releasing an enzyme which melts an atheromatous cap during unstable artheroscelerotic plaque. As described above, the balloon catheter system according to the present embodiment can be extensively employed for ablating not only the origin of arrhythmia but also an unstable artheroscelerotic plaque, cancer cells, a proliferated smooth muscle which causes bronchial asthma or the like.

As described above, the balloon catheter system according to the present embodiment is equipped with the catheter shaft 1 comprising the outer tube 2 and the inner tube 3 which are slidable to each other; the balloon 6 provided between the distal end 4 of the outer tube 2 and a vicinity of the distal end 5 of the inner tube 3; the electrode 7 for delivery of radiofrequency current provided at the center of the balloon 6; the external radiofrequency generator 31 which supplies radiofrequency energy to the electrode 7 for delivery of radiofrequency current via the lead wire 34 to heat the balloon 6; the temperature sensor 8 for detecting the temperature inside the balloon 6; the solution transport path 11 formed between the outer tube 2 and the inner tube 3, in communication with the inside of the balloon 6; the vibration generator 42 which applies a vibrational wave to the balloon 6 through the solution transport path 11 to generate a swirl S inside the balloon 6 and thereby make the temperature of the balloon 6 uniform, and the guide wire 12 which guides the balloon 6 to a target site A. In the balloon catheter system, the temperature sensor 8 is separated from the electrode for delivery of radiofrequency current and is fixed in the vicinity of the distal end 5 of the inner tube 3, thus permitting the temperature of the swirl S flowing along the inner surface of the balloon 6 to be detected.

The vibration generator 42 applies a vibrational wave W to the balloon 6 via the solution transport path 11 to generate a vertical swirl S inside the balloon 6 in relation to the gravity, thereby eliminating a temperature gradient due to convective heat. The temperature sensor 8 fixed in the vicinity of the distal end 5 of the inner tube 3 is capable of detecting the temperature of the swirl S flowing along the inner surface of the balloon 6. Since the temperature of the swirl S flowing along the inner surface of the balloon 6 is approximate to the surface temperature of the balloon 6, an approximate value of the surface temperature of the balloon 6 can be detected by means of detecting the temperature of the swirl S without allowing the temperature sensor 8 to contact with the balloon 6.

Further, the heat insulating material 21 is interposed between the temperature sensor 8 and the electrode 7 for delivery of radiofrequency current. Hence, the temperature sensor 8 can be prevented from being directly heated by the electrode 7 for delivery of radiofrequency current, permitting the temperature of the swirl S approximate to the surface temperature of the balloon to be precisely detected.

Further, the heat insulating material 22 is interposed between the temperature sensor 8 and the inner tube 3 and hence even if the guide wire 12 passing through the inside of the inner tube 3 is heated by radiofrequency electromagnetic coupling, the temperature of the swirl S approximate to the surface temperature of the balloon 6 can be precisely detected by preventing the influence of the heat resulting from the radiofrequency electromagnetic coupling.

Moreover, a heat insulating space 23 is provided between the temperature sensor S and the inner tube 3. Hence, even if the guide wire 12 passing through the inside of the tube 3 is heated by the radiofrequency electromagnetic coupling, the temperature of the swirl S approximate to the surface temperature of the balloon 6 can be precisely detected by preventing the influence of the heat resulting from the radiofrequency electromagnetic coupling.

Furthermore, the temperature sensor 8 is formed into a tubular shape encircling the entire circumference of the inner tube 3, or is equipped with the tubular good thermal conductor 24 encircling the entire circumference of the inner tube 3. Then, the temperature sensor 8 is connected to the tubular good thermal conductor 24 to thereby detect the temperature from the entire circumference of the inner tube 3, enabling the temperature of a swirl S approximate to the surface temperature of the balloon 6 to be precisely detected.

Moreover, the electrode 7 for delivery of radiofrequency current is monopolar or bipolar and when monopolar, a radiofrequency current is applied across the electrode 7 and the counter electrode externally provided, while when bipolar, the same is done across both electrodes. Hence, the electrode 7 for delivery of radiofrequency current can be heated.

Besides, there is provided the electrode temperature sensor 10 for detecting the temperature of the electrode 7 for delivery of radiofrequency current and the electrode temperature sensor 10 is covered with the insulation material 25. Hence, without being affected by a swirl S, the temperature of the electrode 7 for delivery of radiofrequency current can be precisely detected.

Further, the balloon external heat shield knob 26 is provided in contact with the outer surface of the balloon 6 in the vicinity of the distal end 5 of the inner tube 3. Hence, an influence exerted by blood in contact with the balloon 6 is prevented, permitting the temperature of a swirl S approximate to the surface temperature of the balloon 6 to be precisely detected.

Further, as substitute for the electrode 7 for delivery of radiofrequency current and the radiofrequency generator 31, there is provided any one of couples of an ultrasonic heating element and an ultrasonic generator, a laser heating element and laser generator, a diode heating element and diode power supply, and a nichrome wire heating element and nichrome wire power supply unit. Hence, various types of energy can be utilized for heating.

Embodiment 2

Figure 4:
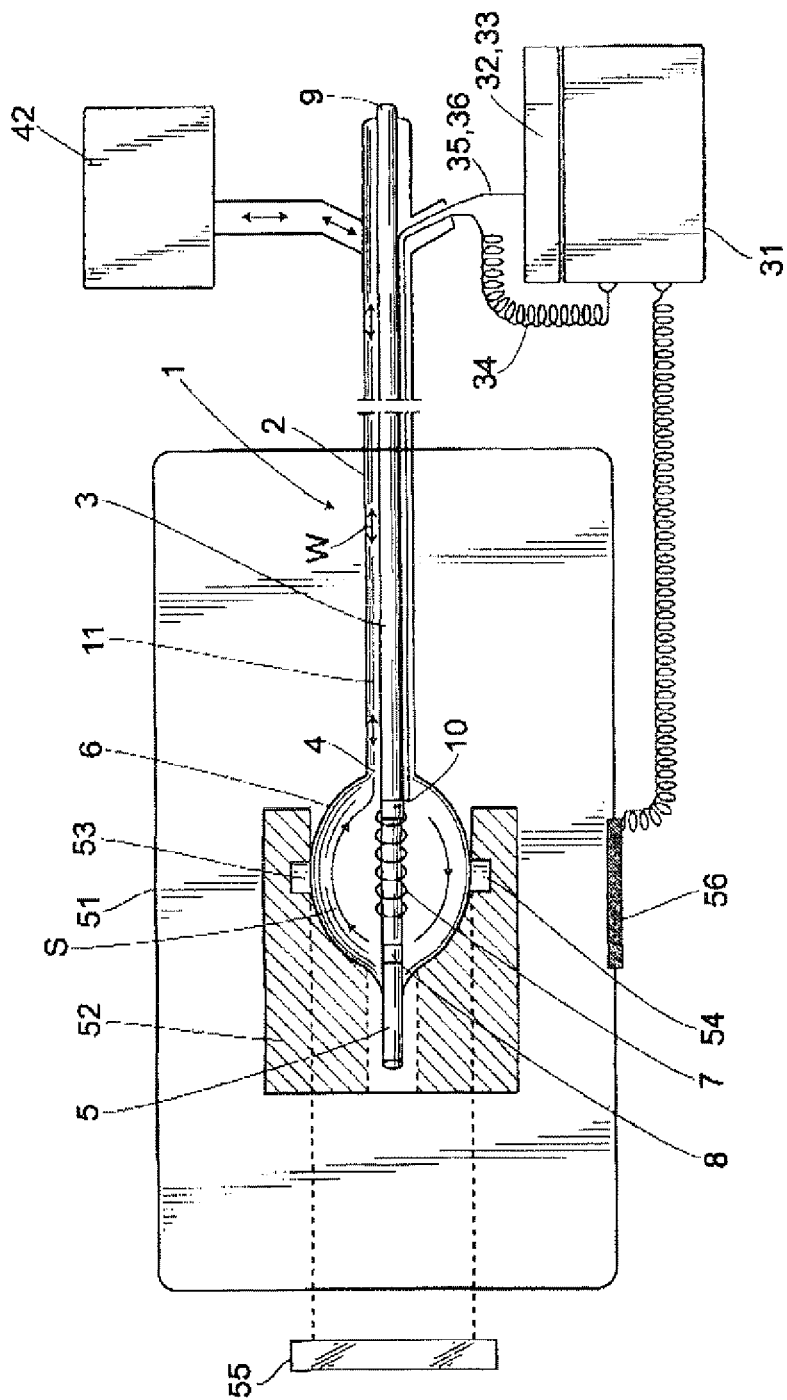
FIG. 4 is a structural view illustrating a device for a phantom experiment in one embodiment of a balloon catheter system according to the present invention.

In the present embodiment, a phantom experiment was practiced using the balloon catheter system according to the embodiment 1. As showing the outline of the phantom experiment in FIG. 4, a phantom 52 with a cylindrical cutout was left inside a bath 51 at 37 degrees C. Temperature sensors 53, 54 were put on upper and lower surfaces of the balloon 6, the electrode 7 for delivery of radiofrequency current was set inside the balloon 6, and the temperature sensor 8 was put at an end of the electrode 7 for delivery of radiofrequency current and in the vicinity of the distal end 5 of the inner tube 3 inside the balloon 6. While applying a radiofrequency current from the external radiofrequency generator 31, an asymmetric vibrational wave W was applied from the external vibration generator 42 to the inside of the balloon 6 via the solution transport path 11 and then the inside of the balloon 6 was agitated by swirls S. In addition, numeral 55 denotes a thermometer for displaying temperatures detected by the temperature sensors 53, 54 and numeral 56 denotes a counter electrode externally provided to apply a radiofrequency current to the electrode 7 for delivery of radiofrequency current. The temperatures detected by the temperature sensors 53, 54 and the electrode temperature sensor 10 were recorded with time.

Figure 5:
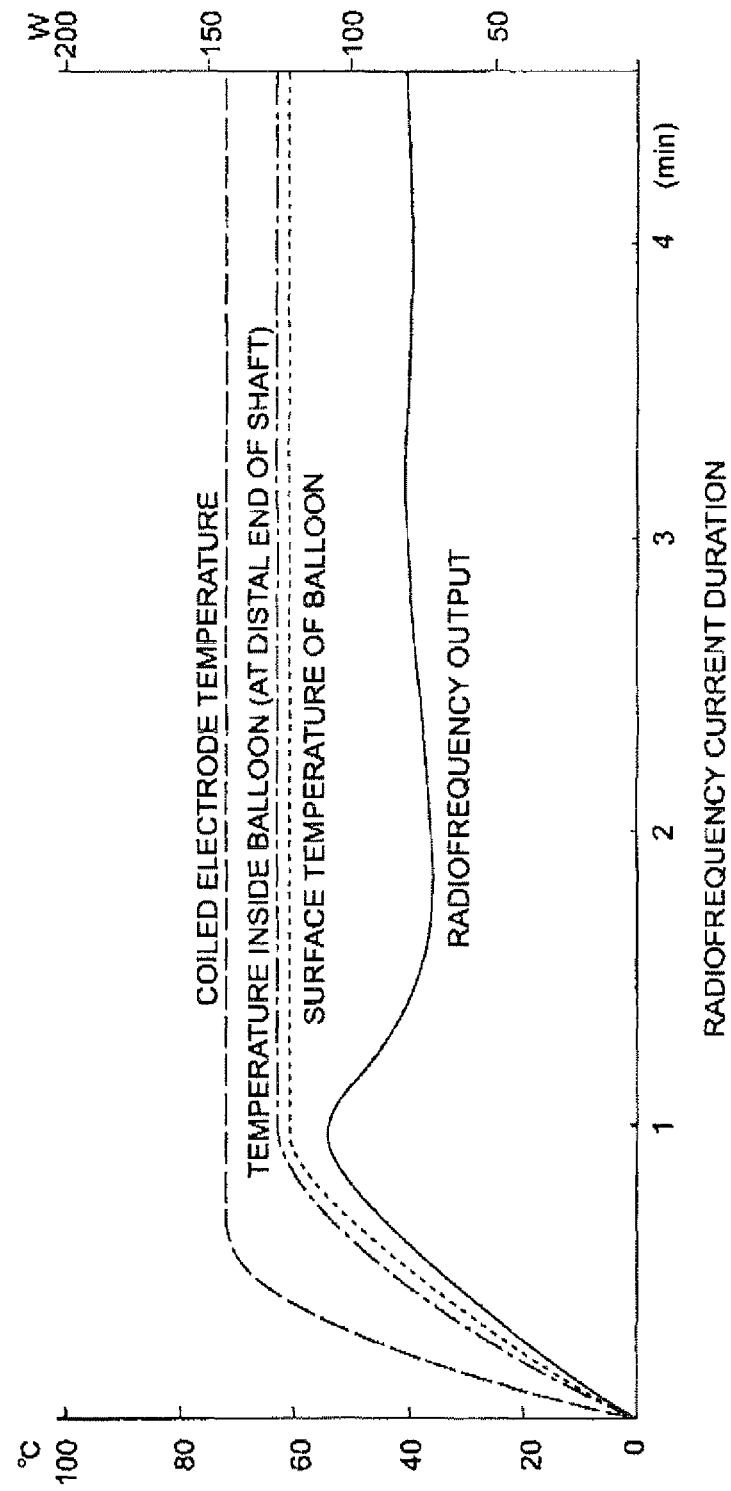
FIG. 5 is a graph illustrating a temperature change in phantom experiment in one embodiment of a balloon catheter system according to the present invention.

As shown in FIG. 5, when applying a radiofrequency current, the temperature of the electrode 7 for delivery of radiofrequency current rose with the passage of time and reached 70 degrees C., while the upper and lower surface temperatures of the balloon 6 reached 60 degrees C. At this time, the temperature sensor 8 put in the vicinity of the distal end 5 of the inner tube 3 inside the balloon 6 indicated 61 degrees C., exhibiting a very near temperature to the surface temperature of the balloon 6.

Figure 6:
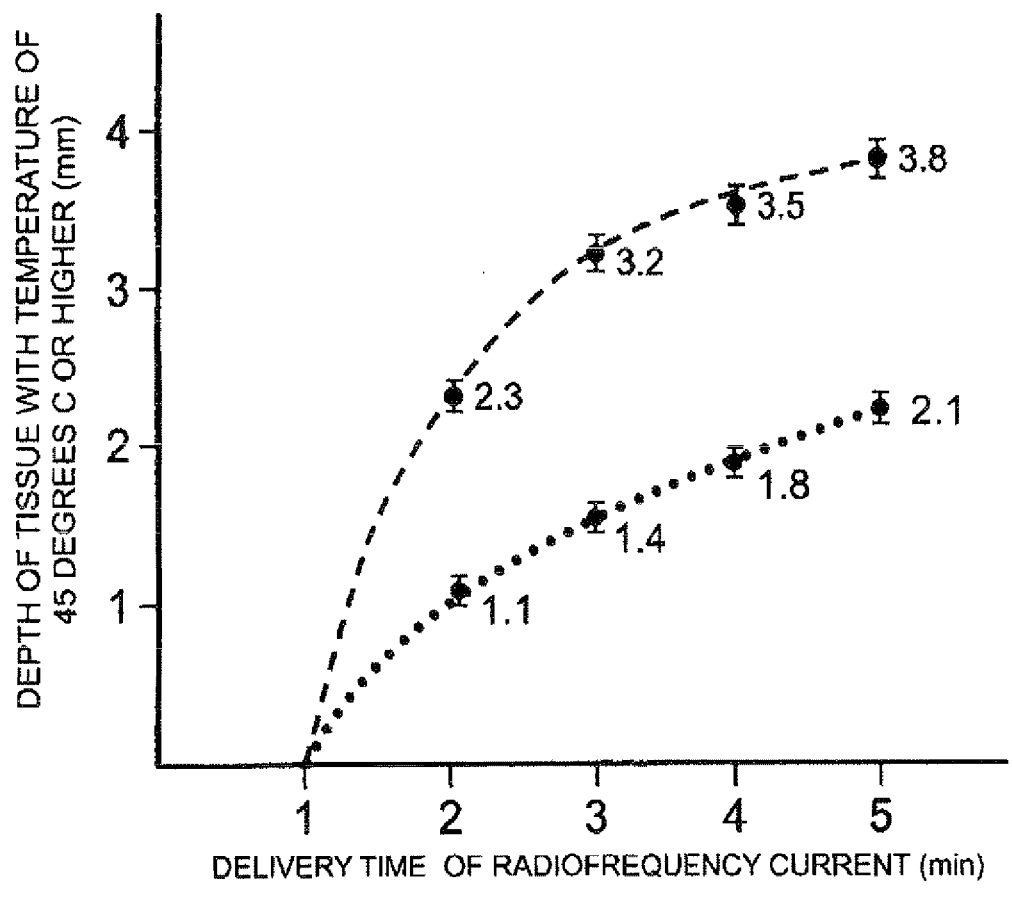
FIG. 6 is a graph illustrating a depth of a tissue at 45 or more degrees C. in a phantom experiment in one embodiment of a balloon catheter system according to the present invention.

In FIG. 6, shown is the relationship between the delivery time of radiofrequency current and a depth where the temperature of tissue showed 45 or more degrees C., when the surface temperature of the balloon 6 is 50 or 60 degrees C. Like this, the longer the delivery time, the deeper the depth where the temperature of tissue reached 45 degrees C. at which the tissue becomes irreversibly damaged. Accordingly, it has been confirmed that by regulating the delivery time of radiofrequency current, an ablation depth was adjustable.

Embodiment 3

Figure 7:
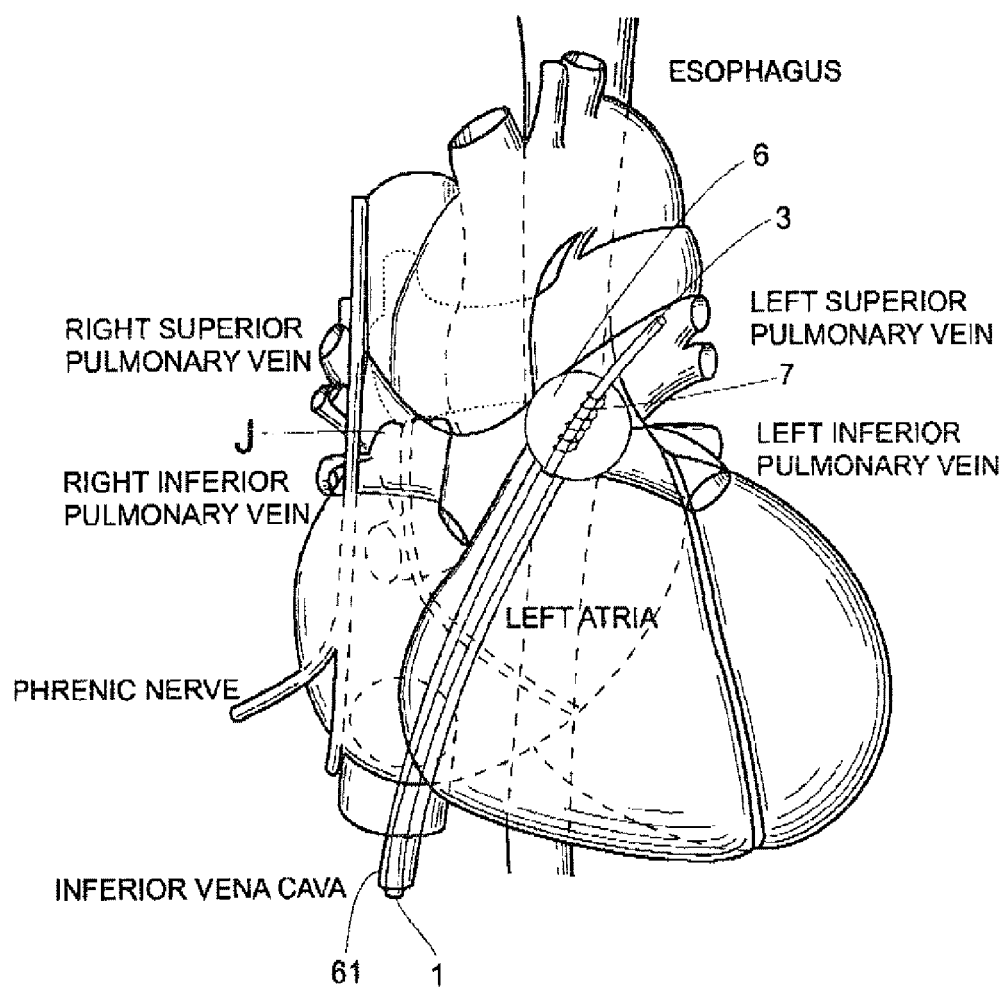
FIG. 7 is a partially enlarged view in the vicinity of the balloon illustrating a usage state in a therapy directed at a source origin of atrial fibrillation in one embodiment of a balloon catheter system according to the present invention.

In the present embodiment, explained is a method for treating a source origin of atrial fibrillation using the balloon catheter system according to the embodiment 1. As showing the outline in FIG. 7, the balloon 6 is allowed to contact with a periphery of an orifice of a pulmonary vein, being the origin of atrial fibrillation, from an inner surface of the vein to treat atrial fibrillation. At this time, an esophagus, phrenic nerves and abdominal vagus nerves exist in the vicinity of the heart and hence it is important that an atrial wall is ablated transmurally without injuring these internal organs and then the application of a radiofrequency current is interrupted. The thermal damage of the tissue becomes irreversible if subjected to the temperature of 45 or more degrees C. and therefore it is important that the surface temperature of the balloon 6 is more precisely monitored and besides the delivery time of radiofrequency current is taken account of.

The catheter shaft 1 is inserted from a femoral vein into a left atrium using a guide sheath 61 and the guide wire 12 and then the balloon 6 dilated by a mixed solution of physiologic saline and a contrast medium, which has been introduced from the solution transport path 11, is wedged into a pulmonary vein vestibule. While applying a radiofrequency current to the electrode 7 for delivery of radiofrequency current inside the balloon 6, an asymmetric vibrational wave W is fed from the vibration generator 42 to the inside of the balloon 6 via the solution transport path 11 to form swirls S. At this time, since the temperature sensor 8 detects the temperature approximate to the surface temperature of the balloon 6, a radiofrequency output is increased until this temperature reaches a preset temperature.

Usually, in the surface temperature of the balloon 6 required to ablate tissue, 60 to 65 degrees C. are most suitable. A radiofrequency current is applied for 2 to 5 minutes depending on the thickness of an atrial wall measured by an intracardiac echo. As shown in FIG. 6, when the surface temperature of the balloon 6 is at 60 degrees C., a tissue depth is 2.3 mm where its temperature reaches 45 degrees C. as a result of the radiofrequency current application for 2 minutes, an application of the current for 3 minutes attains a 3.2 mm depth and 5 minutes for 3.7 mm depth. Thus, atrial walls different in thickness can be ablated with the atrial walls penetrated. Besides, during the application of the current, the safety can be enhanced by monitoring the maximum temperature inside the balloon 6 by means of the electrode temperature sensor 10.

After ablation, the inner tube 3 is stretched in relation to the outer tube 2 to contract the balloon 6, and then the catheter shaft 1 is extracted from the guide sheath 61 to check whether thrombus and fibrin are absent or not on the surface of the balloon 6. Ordinarily, if the surface temperature of the balloon 6 does not exceed 80 and 70 degrees C., respectively, these are absent.

Embodiment 4

Figure 8:
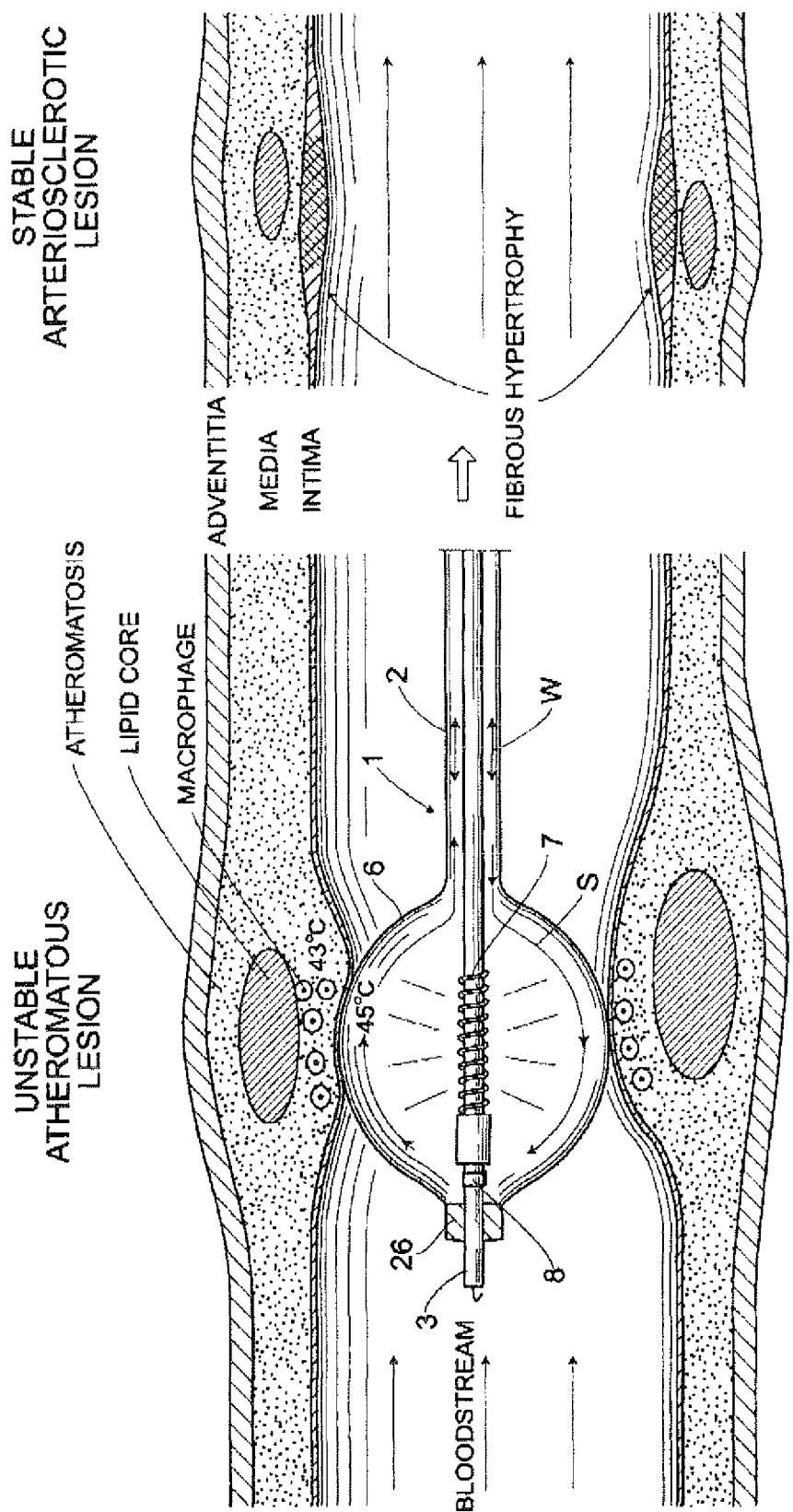
FIG. 8 is a partially enlarged view in the vicinity of the balloon illustrating a usage state in a therapy directed at an unstable atherosclerotic plaque in one embodiment of a balloon catheter system according to the present invention.

In the present embodiment, a description is given for a method for treating an unstable atherosclerotic plaque using the balloon catheter system according to the embodiment 1. As showing the outline in FIG. 8, in a site of the unstable atherosclerotic plaque, macrophages infiltrate underneath a thin atheromatous cap and release a lytic enzyme to lyse the atheromatous cap and hence the atheroma ruptures toward an intravascular lumen to cause an acute arterial occlusion, leading to myocardial infarction or cerebral infarction.

By way of the prevention of acute arterial occlusion, after having photographed a culprit artery from a peripheral vessel using a contrast medium, an angioscope and an ultrasonic catheter are inserted into a vessel to observe a cross section of the vessel to picture the unstable plaque. Then, the catheter shaft 1 is inserted into the site of the unstable plaque to dilate the balloon 6, a vibration generator 42 is allowed to operate, and while a radiofrequency current is delivered under monitoring an approximate value of the surface temperature, detected by the temperature sensor 8, of the balloon 6. When regulating radiofrequency output power so that the approximate value of the surface temperature of the balloon 6 indicates 45 degrees C., the temperature inside the atheromatosis near the atheromatous cap rises to 43 degrees C. and then the application of a radiofrequency current for 2 minutes enables the macrophages to be annihilated. Then, an inflammatory reaction is slightly generated in the site due to heating to accelerate fibrosis and the atheromatous cap is thickened due to fibrous tissue, thus stabilizing the site of the lesion.

Embodiment 5

Figure 9:
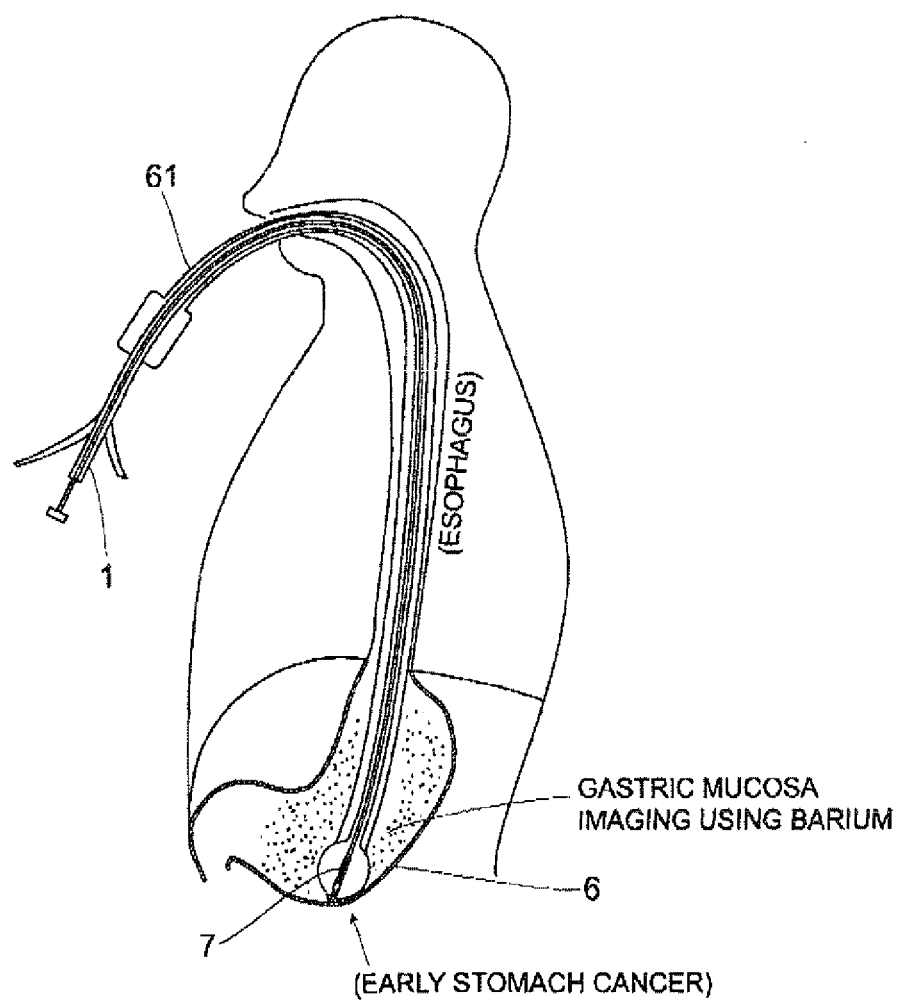
FIG. 9 is a partially enlarged view in the vicinity of the balloon illustrating a usage state in a therapy directed at stomach cancer in one embodiment of a balloon catheter system according to the present invention.
Figure 10:
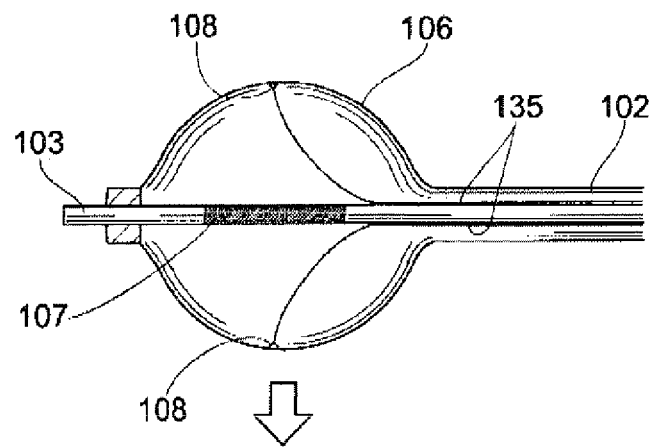
FIG. 10 is a partially enlarged view in the vicinity of the balloon illustrating the traditional balloon catheter system.

In the present embodiment, a description is given for a method for treating stomach cancer using the balloon catheter system according to the embodiment 1. As showing the outline in FIG. 9, when having detected an early stomach cancer by endoscopic examination, a barium examination is performed to clarify the extent of the stomach cancer under fluoroscopy. A guide sheath 61 is inserted into the site of the stomach cancer through a nasal aperture or a mouth and then the catheter shaft 1 is inserted thereinto through the guide sheath 61. Then, depending on a size of the stomach cancer, the balloon 6 is dilated by a mixed solution of a contrast medium and a physiological saline to be pressed against the site of the stomach cancer and then the balloon 6 is heated. When the site is shallow, short-time heating is performed with the temperature inside the balloon 6 kept at 45 degrees C., while when deep, long-time heating is done with the higher temperature inside the balloon 6.

In addition, the present invention is not limited to the above embodiments and various modifications are possible within the scope of the gist of the present invention. The form of the balloon, e.g., is not limited to one described above and various forms may be applicable depending on the organ to be treated.

What is claimed is:

1. A balloon catheter system comprising:
   a catheter shaft comprising an outer tube and an inner tube which are slidable to each other;
   a balloon provided between a distal end of said outer tube and a vicinity of a distal end of said inner tube;
   an electrode for delivery of radiofrequency current provided in a central portion of said balloon,
   an external radio frequency generator which supplies radiofrequency energy to said electrode for delivery of radiofrequency current through a lead wire to heat said balloon;
   an external thermometer which detects a temperature through a temperature sensor inside said balloon and a lead wire of said temperature sensor;
   a solution transport path formed between said outer tube and said inner tube, in communication with an inside of said balloon;
   an external vibration generator which applies a vibrational wave to an inside of said balloon through said solution transport path and generates swirls S inside said balloon to make temperature inside said balloon uniform; and
   a guide wire which guides said balloon to a target site,
   wherein said temperature sensor is separated from said electrode for delivery of radiofrequency current and is fixed to said distal end of said inner tube inside said balloon to detect the temperature of swirls flowing along an inner surface of said balloon, where a heat insulating material is interposed between said temperature sensor for detecting the temperature of swirls flowing along the inner surface of said balloon and said electrode for delivery of radiofrequency current provided in the central portion of said balloon.

2. A balloon catheter system according to claim 1, wherein a heat insulating material is interposed between said temperature sensor and said inner tube.

3. A balloon catheter system according to claim 1, wherein a thermal insulating space is interposed between said temperature sensor and said inner tube.

4. A balloon catheter system according to claim 1, wherein said temperature sensor is formed in a tubular shape encircling an entire circumference of said inner tube or is equipped with a tubular good thermal conductor encircling said entire circumference of said inner tube and said temperature sensor is connected to said tubular good thermal conductor.

5. A balloon catheter system according to claim 1, wherein said electrode for delivery of radiofrequency current is monopolar or bipolar and when bipolar, a radiofrequency current is applied across said electrode, while when monopolar, a radiofrequency current is applied across said electrode and a counter electrode externally provided.

6. A balloon catheter system according to claim 1, comprising:
   an electrode temperature sensor which detects a temperature of said electrode for delivery of radiofrequency current and is covered with an insulating material.

7. A balloon catheter system according to claim 1, comprising:
   a balloon external heat shield knob arranged in the vicinity of a distal end of said inner tube, in contact with an outer surface of said balloon.

8. A balloon catheter system according to claim 1,
   wherein as substitute for said electrode for delivery of radiofrequency current and said radiofrequency generator, said balloon catheter system is equipped with any one of couples of:
   an ultrasonic heating element and an ultrasonic generator,
   a laser heating element and a laser generator,
   a diode heating element and a diode power supply unit, and
   a nichrome wire heating element and a nichrome wire power supply unit.

* * * * *